(12) United States Patent
Vidal et al.

(10) Patent No.: US 11,090,350 B2
(45) Date of Patent: Aug. 17, 2021

(54) AQUEOUS FORMULATION COMPRISING A LIPOPHILIC COMPOSITION

(71) Applicant: EVERGREEN LAND LIMITED, Central Hong Kong (HK)

(72) Inventors: Nicolas Vidal, Marseilles (FR); Jean-Francois Lesgards, Marseilles (FR)

(73) Assignee: Evergreen Land Limited, Central (HK)

( * ) Notice: Subject to any disclaimer, the term of this patent is extended or adjusted under 35 U.S.C. 154(b) by 847 days.

(21) Appl. No.: 15/401,627

(22) Filed: Jan. 9, 2017

(65) Prior Publication Data

US 2017/0196925 A1    Jul. 13, 2017

(30) Foreign Application Priority Data

Jan. 8, 2016   (FR) ...................................... 1650158

(51) Int. Cl.

| | |
|---|---|
| *A61K 36/61* | (2006.01) |
| *A01N 25/04* | (2006.01) |
| *A61K 9/00* | (2006.01) |
| *A61K 47/44* | (2017.01) |
| *A61K 9/06* | (2006.01) |
| *A61K 8/26* | (2006.01) |
| *A01N 31/06* | (2006.01) |
| *A01N 25/02* | (2006.01) |
| *A01N 65/28* | (2009.01) |
| *A61K 8/34* | (2006.01) |
| *A61K 8/67* | (2006.01) |
| *A61K 8/73* | (2006.01) |
| *A61K 8/92* | (2006.01) |
| *A61K 8/96* | (2006.01) |
| *A61K 47/02* | (2006.01) |
| *A61K 47/10* | (2017.01) |
| *A61K 47/22* | (2006.01) |
| *A61K 47/38* | (2006.01) |
| *A61Q 19/00* | (2006.01) |

(52) U.S. Cl.
CPC .............. *A61K 36/61* (2013.01); *A01N 25/02* (2013.01); *A01N 25/04* (2013.01); *A01N 31/06* (2013.01); *A01N 65/28* (2013.01); *A61K 8/26* (2013.01); *A61K 8/34* (2013.01); *A61K 8/345* (2013.01); *A61K 8/678* (2013.01); *A61K 8/731* (2013.01); *A61K 8/922* (2013.01); *A61K 8/965* (2013.01); *A61K 9/0014* (2013.01); *A61K 9/06* (2013.01); *A61K 47/02* (2013.01); *A61K 47/10* (2013.01); *A61K 47/22* (2013.01); *A61K 47/38* (2013.01); *A61K 47/44* (2013.01); *A61Q 19/00* (2013.01); *A61K 2800/10* (2013.01); *A61K 2800/52* (2013.01); *A61K 2800/522* (2013.01); *A61K 2800/524* (2013.01); *A61K 2800/592* (2013.01)

(58) Field of Classification Search
None
See application file for complete search history.

(56) References Cited

U.S. PATENT DOCUMENTS

2003/0216283 A1\* 11/2003 Ishida .................... A61K 8/345
512/25
2013/0324461 A1\* 12/2013 Sitkovsky .............. A61K 45/06
514/4.9

FOREIGN PATENT DOCUMENTS

| EP | 1699429 A1 | 9/2006 |
|---|---|---|
| FR | 2974312 A1 | 10/2012 |
| JP | 55162710 A | 12/1980 |

\* cited by examiner

*Primary Examiner* — Terry A McKelvey
*Assistant Examiner* — Catheryne Chen
(74) *Attorney, Agent, or Firm* — Bachman & LaPointe, P.C.

(57) ABSTRACT

An aqueous formulation comprising between 0.1% and 50% by weight of lipophilic composition, said formulation further comprising between 0.1% and 10% by weight of homogenising component comprising at least microcrystalline cellulose; between 0.01% and 2% by weight of clay; and the remainder in water.

24 Claims, No Drawings

AQUEOUS FORMULATION COMPRISING A LIPOPHILIC COMPOSITION

BACKGROUND OF THE INVENTION

The present invention relates to an aqueous formulation comprising between 0.1% and 50% by weight of lipophilic composition, for example an essential oil or a mixture of essential oils.

It applies in particular to an aqueous formulation for cosmetic and/or pharmaceutical use, the lipophilic composition, for example an essential oil or a mixture of essential oils, then having properties corresponding to the cosmetic and/or pharmaceutical effect sought, for example a repelling function for harmful animals, a therapeutic and/or prophylactic function, for example a soothing function intended to ease stings or bites of harmful animals, an anti-burn function, a healing function, a relaxing function or an anti-inflammatory function, or a wellbeing function such as a perfuming function, a deodorant function, a biocidal function, a bactericidal function or a fungicidal function.

Such formulations are generally intended to be used either by direct application to the skin of the subject, or indirectly in the air or on other surfaces, for example by means of an atomiser, a ball applicator or other application modes.

Since water and lipophilic compositions are immiscible liquids, using emulsifying agents, in particular synthetics, is known for providing stability of their mixture, all the more so when the lipophilic composition concentration is high.

However, the synthetic nature of these emulsifying agents poses a problem, in particular in the context of a cosmetic and/or pharmaceutical use of the formulation. Indeed, their presence in the formulation may alter the properties of the lipophilic composition, in particular the perfuming properties, but also cause undesirable skin reactions, in particular irritations or allergies, in certain subjects.

In order to overcome these drawbacks, an aqueous formulation for cosmetic use is known from the document JP-S55/162710, comprising water and a high concentration (up to 85% by weight) of oil(s), as well as a homogenising mixture comprising in particular microcrystalline cellulose, optionally supplemented with a water-soluble polymer, for example based on carboxymethylcellulose, in order to limit as far as possible the use of synthetic emulsifiers.

However, this formulation does not give complete satisfaction, in that it does not make it possible to completely stabilise the water-oil(s) mixture. Because of this, the formulation may, after as certain length of time, exhibit a phase separation between the water and the oil(s), which may cause problems of distribution of the active element formed by said oil(s) within the container of said formulation and/or on the part of the body of the subject on which said formulation is applied, and thus impair the efficacy of said formulation.

To improve the stability, in particular over time, of an aqueous formulation comprising a high concentration of oil(s), the document FR-2 974 312 proposes adding cellulose nanocrystals to such a formulation, but this solution proves to be relatively complex to implement.

In addition, an aqueous formulation for cosmetic use is known from the document EP-1 699 429, comprising water and a high concentration (at least 30% by weight) of lipophilic composition based on perfumed oil(s), in particular essential oil(s), as well as a small quantity (between 0.1% and 4% by weight) of a cellulose derivative, in particular carboxymethylcellulose, and/or a clay, in particular bentonite.

However, in this document, adding bentonite and/or cellulose derivative aims mainly to thicken the formulation, whereas the stabilisation of the aqueous formulation is obtained by the addition of an emulsifier. Moreover, the quantity of thickening agent makes the formulation difficult to apply, in particular by means of an atomiser.

SUMMARY OF THE INVENTION

The invention aims to improve the prior art by proposing in particular an aqueous formulation comprising water and a high concentration of lipophilic composition, in which the mixture of water and lipophilic composition has improved homogeneity and stability over time while being easy to apply, in particular by means of an atomiser or a ball applicator, to the skin of a subject, said formulation furthermore being easy to manufacture.

To this end, the invention proposes an aqueous formulation comprising between 0.1% and 50% by weight of lipophilic composition, said formulation further comprising:
 between 0.1% and 10% by weight of homogenising component comprising at least microcrystalline cellulose;
 between 0.01% and 2% by weight of clay;
 the remainder in water.

Other particularities and advantages of the invention will appear in the following description of various particular embodiments.

DETAILED DESCRIPTION

The invention relates to a formulation comprising between 0.1% and 50% by weight of lipophilic composition, said lipophilic composition comprising in particular at least one oil, and more particularly an essential oil or a mixture of essential oils. In particular, the invention relates to a formulation comprising a high concentration, in particular more than 20% by weight, of a lipophilic composition.

The invention applies in particular to an aqueous formulation for cosmetic and/or pharmaceutical use, the lipophilic composition then having properties corresponding to the cosmetic and/or pharmaceutical effect sought.

In particular, the lipophilic composition may have a repellent function for harmful animals. To this end, the lipophilic composition may for example comprise p-menthane-3,8-diol (PMD), which is a natural ingredient that is particularly effective in repelling stinging or biting haematophagous insects such as mosquitoes or tics. According to one embodiment, at least 10%, and in particular more than 40%, by weight of PMD is present in the lipophilic composition.

By way of example, the lipophilic composition may comprise essential oil derived from lemon-scented eucalyptus or citronella, such as for example the essential oils sold under the trade marks Citrepel® and Citriodiol®, such oils constituting known natural sources of p-menthane-3,8-diol.

The lipophilic composition may also have other functions, in particular therapeutic and/or prophylactic functions such as soothing functions intended to ease stings or bites of harmful animals, anti-burn, healing, relaxing or anti-inflammatory functions, or wellbeing functions such as perfuming, deodorant, biocidal, bactericidal or fungicidal functions.

The aqueous formulation further comprises between 0.1% and 10% by weight, and in particular between 0.1% and 2% by weight, of homogenising component comprising at least microcrystalline cellulose, in order to improve the distribution of the lipophilic composition in water.

In particular, the microcrystalline cellulose is an ingredient of natural origin, in particular issuing from wood, which is organised in clusters to a macroscopic scale. Moreover, it is insoluble in water, and forms a gel by generating solid-solid bonds between the water and the lipophilic composition when it is added to the aqueous formulation.

According to one embodiment, the homogenising component further comprises carboxymethylcellulose, xanthan gum or a mixture of these compounds, the xanthan gum having in particular thickening and gelling properties. In particular, microcrystalline cellulose can be co-processed with carboxymethylcellulose and/or with xanthan gum when the homogenising component is manufactured.

Particularly advantageously, the homogenising component comprises a mixture of microcrystalline cellulose with carboxymethylcellulose and/or xanthan gum, said mixture comprising in particular between 75% and 95% by weight of microcrystalline cellulose and between 5% and 25% by weight of carboxymethylcellulose and/or xanthan gum.

Furthermore, the aqueous formulation comprises between 0.01% and 2% by weight, in particular less than 1% by weight, and more particularly less than 0.5% by weight, of clay, in order to stabilise the mixture of water and lipophilic composition over time, and thus to prevent phase separation and problems of homogeneity and distribution of the lipophilic composition that may stem therefrom, in particular during the application of said formulation to the skin of a subject. Moreover, the small quantity of clay allows to limit the thickening of the formulation, and thus to facilitate application thereof, in particular by means of a standard atomiser or a ball applicator.

In particular, the clay may comprise a smectite, in particular by comprising bentonite, or other families of clays such as kaolinite, illite, chlorite, vermiculite, sepiolite or attapulgite. Advantageously, the clay may comprise bentonite with a purity close to 100% by mass, and containing less than 10% by weight of total crystalline silica.

The aqueous formation may further comprise other ingredients, in particular in order to confer additional properties thereon.

Thus the aqueous formulation may comprise between 0.1% and 50%, in particular between 5% and 20%, by weight of perfuming composition. In particular, the perfuming composition may comprise an essential oil or a mixture of essential oils, or other ingredients in particular extracted from essential oils, such as esters or terpenes.

For example, the perfuming composition may be based on Iceberg 57656® or RS57656®.

Moreover, the formulation may also comprise:
  less than 20% by weight of preservative agent, for example a quantity of between 0.4% and 5% by weight of phenethyl alcohol of natural origin;
  less than 10% by weight of antioxidant agent, for example a quantity of less than 1% by weight of vitamin E;
  less than 2% by weight of pH rectifier agent, in particular based on citric acid, for adjusting the pH of said formulation over a range of between 3 and 7, preferably close to the pH of skin;
  between 3% and 50%, in particular less than 10%, by weight of one or more solvents, said solvent(s) or solvents being non-assimilable to lipophilic components or to surfactant agents, and in particular chosen from alcohols, acids and/or acid salts. In particular, the solvent(s) may be chosen from ethanol, isopropanol, methylenediol, ethylene glycol, propanediol, glycerol, butanediol, pentanol, isopentyldiol, hexanol, hexanediol and benzanediol.

Finally, whatever the composition of the aqueous formulation, in particular with regard to the quantities of lipophilic composition, homogenising mixture, clay, and other possible ingredients, the remainder of said formulation to 100% is water, in particular demineralised water.

In particular, the aqueous formulation may be manufactured in accordance with a simple method that provides for the following steps:
  mixing the lipophilic composition, the homogenising component, the clay eventual perfuming, preservative, antioxidant and/or pH rectifier agents;
  mechanical agitation of said mixture, in particular by means of a rotor-stator functioning at a speed of 3000 rpm, for a period of approximately 10 minutes;
  resting the formulation obtained, for a period of between 10 and 30 minutes.

Moreover, if the aqueous formulation to be obtained also comprises a solvent, the manufacturing method may, after the aforementioned resting, provide for the following supplementary steps:
  adding said solvent to said formulation; and
  mechanical agitation of said formulation, in particular by means of a rotor-stator functioning at a speed of 3000 rpm, for a period of approximately 5 minutes.

EXAMPLES

During a test procedure carried in a laboratory, nine samples of aqueous formulations were prepared, in particular in accordance with a method as described above, and said samples all comprised demineralised water, as well as:
  26% by weight of lemon-scented eucalyptus essential oil of the Citrepel® type;
  13% by weight of perfuming composition of the Iceberg 57656® type;
  3.5% by weight of glycerol;
  0.25% by weight of vitamin E, sold under the trade mark Bioxan®;
  up to 0.02% by weight of citric acid.

Moreover, each of these samples comprised:
for samples 1, corresponding to test samples of the formulation proposed by the invention;
  sample 1a: 1% by weight of microcrystalline cellulose and 0.2% by weight of bentonite;
  sample 1b: 1% by weight of homogenising mixture based on microcrystalline cellulose co-processed with carboxymethylcellulose and 0.2% by weight of bentonite, said homogenising mixture comprising approximately 85% by weight of microcrystalline cellulose and approximately 15% by weight of carboxymethylcellulose;
for sample 2: 0.2% by weight of bentonite;
for sample 3: 1% by weight of homogenising mixture based on microcrystalline cellulose and carboxymethylcellulose;
for sample 4: 1% by weight of xanthan gum and 0.2% by weight of bentonite;
for sample 5: 1% by weight of carboxymethylcellulose;
for sample 6: 1% by weight of carboxymethylcellulose and 0.2% by weight of bentonite;
for sample 7: 1% by weight of homogenising mixture based on microcrystalline cellulose and xanthan gum;
for sample 8: 11% by weight of homogenising mixture based on microcrystalline cellulose and carboxymethylcellulose and 2.5% by weight of bentonite, said homogenising mixture comprising approximately 85% by weight of microcrystalline cellulose and approximately 15% by weight of carboxymethylcellulose.

Next, these nine samples were all subjected to efficacy tests in order to evaluate respectively their stability over time, in particular by means of a phase-separation test at 54° C. for 24 hours, and their dispensing by atomisation.

Following these tests, the results obtained were as follows:
with regard to the phase-separation test, only the test samples 1a, 1b had satisfactory results;
with regard to the test for dispensing by atomisation, only samples 1a, 1b, 2 and 3 had satisfactory results.

Thus these tests allowed to demonstrate, because of the good results obtained by test samples 1a, 1b, the efficacy of the simultaneous addition of bentonite and of a homogenising mixture based on microcrystalline cellulose, and this in appropriate quantities, to guarantee both stability over time and good dispensing by atomisation of an aqueous formulation comprising a high concentration of lipophilic composition.

Indeed, the good results of test samples 1a, 1b, in terms of both stability over time and dispensing by atomisation, showed the efficacy of the combined presence of microcrystalline cellulose and bentonite in an aqueous formulation rich in lipophilic composition, in particularly in comparison with the results obtained by sample 5, which contained 1% of carboxymethylcellulose, and was in particular devoid of bentonite and microcrystalline cellulose.

Furthermore, the results obtained by sample 2, which contained bentonite in proportions corresponding to that of the invention (0.2%), but was devoid of microcrystalline cellulose, showed that, though the presence of bentonite alone in such proportions in an aqueous formulation rich in essential oil(s) made it possible to obtain satisfactory results in terms of dispensing by atomisation, it was however not sufficient to guarantee good stability over time, since this formulation exhibited a relatively significant phase separation between water and lipophilic composition after the phase-separation test.

Likewise, the results obtained by sample 3, which contained a mixture of microcrystalline cellulose and carboxymethylcellulose in proportions corresponding to that of the invention (1%), but was devoid of bentonite, showed that, though the presence of this mixture alone in such proportions in an aqueous formulation rich in lipophilic composition also made it possible, like sample containing only bentonite, to obtain good results in terms of dispensing by atomisation, it also did not suffice to guarantee good stability over time.

Moreover, the result obtained by test sample 1b, which contained 1% of microcrystalline cellulose/carboxymethylcellulose mixture and 0.2% of bentonite, compared with those obtained by sample 6, which also contained 0.2% of bentonite, but 1% of homogenising mixture solely based on carboxymethylcellulose, showed the increased efficacy of the addition of microcrystalline cellulose in judiciously chosen proportions, and that in terms of both dispensing by atomisation and stability over time.

In addition, the results obtained by test sample 1a, which contained 1% of homogenising mixture solely based on microcrystalline cellulose and 0.2% of bentonite, allowed to show, by comparison with the results obtained with sample 6, the efficacy of the simple combination of microcrystalline cellulose and bentonite, and that in judiciously chosen proportions, in terms of both dispensing by atomisation and stability over time.

Furthermore, the results obtained by sample 4, which contained bentonite combined with an ingredient other than microcrystalline cellulose (xanthan gum), as well as the results obtained by sample 7, which contained microcrystalline cellulose combined with an ingredient other than bentonite (xanthan gum), showed the increased efficacy of the combined presence of bentonite and microcrystalline cellulose compared with the combined presence of one or other of these ingredients with other types of ingredient, in terms of both stability over time and dispensing by atomisation.

Finally, the results obtained by sample 8, which contained, just like test samples 1a, 1b, both bentonite and a homogenising mixture based on microcrystalline cellulose, but in different proportions, and in particular higher than those of said test samples (11% for the mixture based on microcrystalline cellulose and 2.5% for bentonite), showed that the combined presence of these two ingredients in an aqueous formulation rich in a lipophilic composition was by itself not sufficient to guarantee good stability over time, nor good dispensing by atomisation, and that these two ingredients necessarily had to be added at judiciously chosen proportions to guarantee good results.

What is claimed is:

1. An aqueous formulation comprising between 0.1% and 50% by weight of lipophilic composition, said formulation comprising:
   between 0.1% and 10% by weight of homogenising component comprising at least microcrystalline cellulose;
   between 0.01% and 2% by weight of clay; and
   water, wherein the aqueous formulation is homogenized.

2. The aqueous formulation according to claim 1, wherein the homogenising component further comprises carboxymethylcellulose, xanthan gum or a mixture of these compounds.

3. The aqueous formulation according to claim 1, wherein the clay comprises a smectite.

4. The aqueous formulation according to claim 1, wherein said aqueous formulation comprises more than 20% by weight of lipophilic composition.

5. The aqueous formulation according to claim 1, wherein the lipophilic composition comprises at least one oil.

6. The aqueous formulation according to claim 1, wherein the lipophilic composition has a repellent function for harmful animals.

7. The aqueous formulation according to claim 5, wherein the lipophilic composition comprises p-menthane-3,8-diol (PMD).

8. The aqueous formulation according to claim 1, wherein the lipophilic composition has at least one function chosen from therapeutic and/or prophylactic functions.

9. The aqueous formulation according to claim 1, wherein the aqueous formulation comprises between 0.1% and 2% by weight of homogenising component.

10. The aqueous formulation according to claim 1, wherein the homogenising component comprises a mixture of microcrystalline cellulose and carboxymethylcellulose.

11. The aqueous formulation according to claim 1, wherein the aqueous formulation comprises one of less than 1%, and less than 0.5%, by weight of clay.

12. The aqueous formulation according to claim 1, wherein the aqueous formulation comprises one of between 0.1% and 50%, and between 5% and 20%, by weight of perfuming composition.

13. The aqueous formulation according to claim 12, wherein the perfuming composition comprises one of an essential oil or a mixture of essential oils.

14. The aqueous formulation according to claim 1, wherein the aqueous formulation further comprises less than 20% by weight of a preservative agent.

15. The aqueous formulation according to claim 14, wherein the preservative agent comprises phenethyl alcohol of natural origin.

16. The aqueous formulation according to claim 1, wherein the aqueous formulation further comprises less than 10% by weight of antioxidant agent.

17. The aqueous formulation according to claim 16, wherein the antioxidant agent comprises vitamin E.

18. The aqueous formulation according to claim 1, further comprising less than 2% by weight of pH rectifier agent.

19. The aqueous formulation according to claim 1, further comprising between 3% and 50%, by weight of one or more solvents.

20. The aqueous formulation according to claim 15 wherein preservative agent comprises phenethyl alcohol of natural origin in a quantity of between 0.4% and 5% by weight of said formulation.

21. The aqueous formulation according to claim 17 wherein antioxidant agent comprises vitamin E, in a quantity of less than 1% by weight of said formulation.

22. The aqueous formulation according to claim 18 wherein the rectifier agent is based on citric acid.

23. The aqueous formulation according to claim 19 further comprising less than 10% by weight of one or more solvents.

24. The aqueous formulation according to claim 19 wherein said one or more solvents comprises glycerol.

* * * * *